United States Patent
Kuan et al.

(10) Patent No.: US 6,198,839 B1
(45) Date of Patent: *Mar. 6, 2001

(54) DYNAMIC CONTROL AND DECISION MAKING METHOD AND APPARATUS

(75) Inventors: Chih-Chau L. Kuan, Redmond; Shih-Jong J. Lee, Bellevue; Seho Oh, Mukilteo; Wendy R. Bannister; Michael G. Meyer, both of Seattle, all of WA (US)

(73) Assignee: Tripath Imaging, Inc., Burlington, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/924,351

(22) Filed: Sep. 5, 1997

(51) Int. Cl.$^7$ .................................... G06K 9/00
(52) U.S. Cl. ................ 382/133; 382/224; 128/922
(58) Field of Search .................. 128/920, 923, 128/925, 922; 382/133, 134, 224, 128; 356/92

(56) References Cited

U.S. PATENT DOCUMENTS

| | | |
|---|---|---|
| 4,741,043 | 4/1998 | Bacus . |
| 4,965,725 * | 10/1990 | Rutenberg ............... 128/925 |
| 5,023,785 | 6/1991 | Adrion et al. . |
| 5,235,522 | 8/1993 | Bacus . |
| 5,249,274 | 9/1993 | Sztipanovits et al. . |
| 5,287,272 * | 2/1994 | Rutenberg et al. ........... 128/925 |
| 5,315,700 | 5/1994 | Johnston et al. . |
| 5,341,507 | 8/1994 | Terada et al. . |
| 5,361,140 | 11/1994 | Hayenga et al. . |
| 5,499,097 | 3/1996 | Ortyn et al. . |
| 5,528,703 | 6/1996 | Lee . |
| 5,557,097 | 9/1996 | Ortyn et al. . |
| 5,757,954 * | 5/1998 | Kuan et al. ............... 382/133 |
| 5,797,130 * | 8/1998 | Nelson et al. ............. 382/244 |
| 5,799,101 * | 8/1998 | Lee et al. ................ 382/133 |
| 5,828,776 * | 10/1998 | Lee et al. ................ 382/133 |

OTHER PUBLICATIONS

Davis "Knowledge–Based Cephalometric Analysis: A comparison with Clinicians Using Interactive Computer Methods" Computer and Biomedical Research, vol. 27, pp. 210–218, Sep. 1994.*

(List continued on next page.)

Primary Examiner—Amelia Au
Assistant Examiner—Jingge Wu
(74) Attorney, Agent, or Firm—Hans Sun; Emil Moffa; George Leone

(57) ABSTRACT

Dynamic control of the processing flow of an image analyzer such as a biological specimen analyzer as processing proceeds. Data collected and processed from a specimen under analysis, such as a biological specimen on a microscope slide, determines the fate of further processing. If there is enough evidence, based on the data collected from a slide, to make a decision with sufficient confidence, the processing of the slide can be stopped and a decision may be rendered. By avoiding unnecessary additional computation system throughput may be enhanced. Otherwise, data collection and computation continues until either certain termination criteria are met or no more data is left to acquire. This slide-dependent control and decision making method flexibly limits the amount of computation required to reach a system decision about a specimen. By evaluating analysis processing continuously a maximum signal to noise ratio may be achieved by preventing additional noise from entering the analysis and thus swamping signal information.

14 Claims, 14 Drawing Sheets

OTHER PUBLICATIONS

Hayes–Roth, Barbara, "A Blackboard Architecture for Control", *Artificial Intelligence,* 1985, pp. 251–321.

Hull, Jonathan et al., "A Blackboard–based Approach to Handwritten ZIP Code Recognition", State University of New York at Buffalo, Department of Computer Science, Buffalo, NY 14260, pp. 1018–1032.

Nii, H. Penny, "Part One: Blackboard Systems: The Blackboard Model of Problem Solving and the Evolution of Blackboard Architectures", *The AI Magazine,* Summer 1986, pp. 38–53.

Reexamination Certificate, U.S. Patent B1 4, 741, 043 to Bacus. Certificate issued Aug. 9, 1994.

* cited by examiner

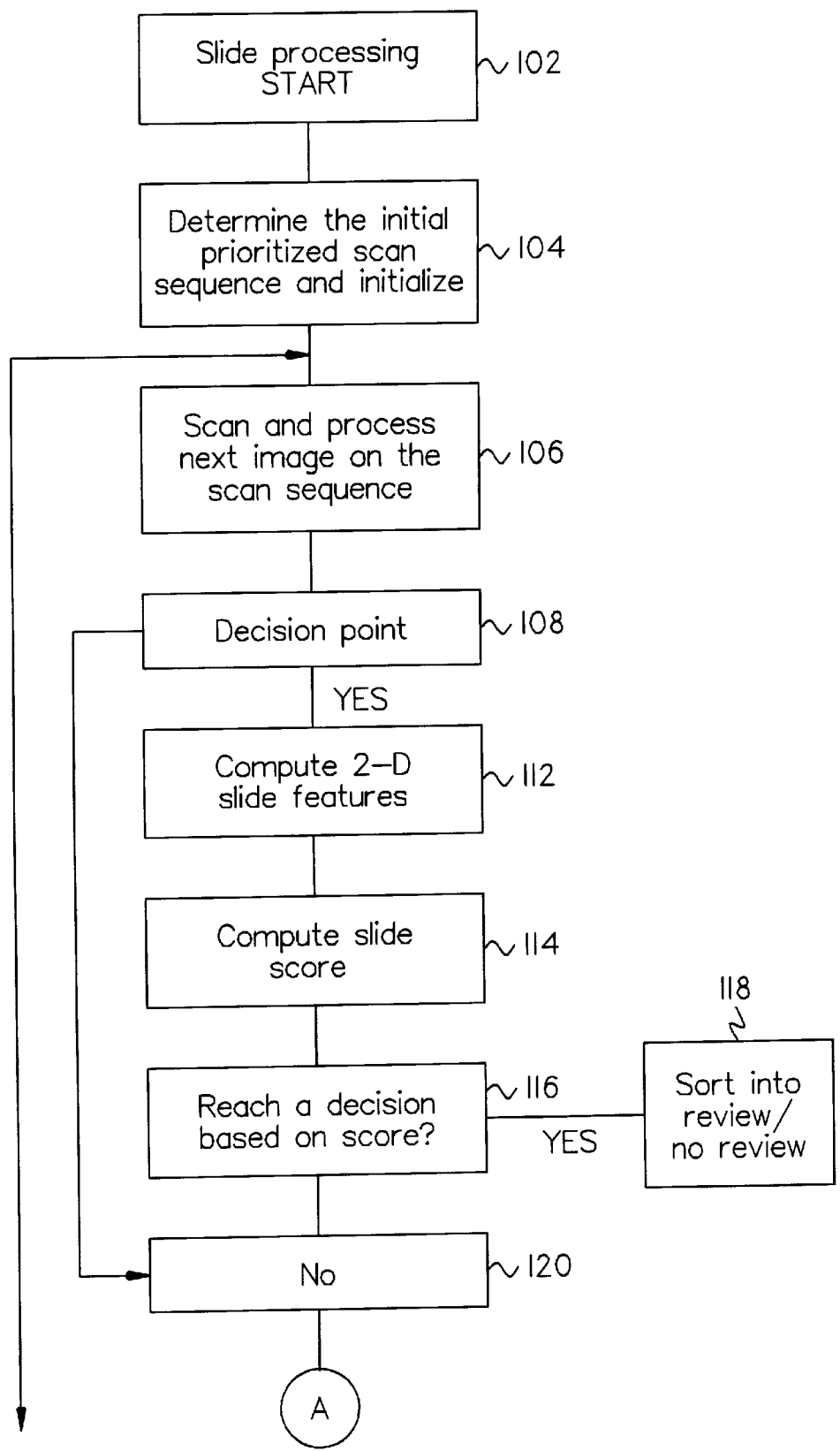
Fig_2A

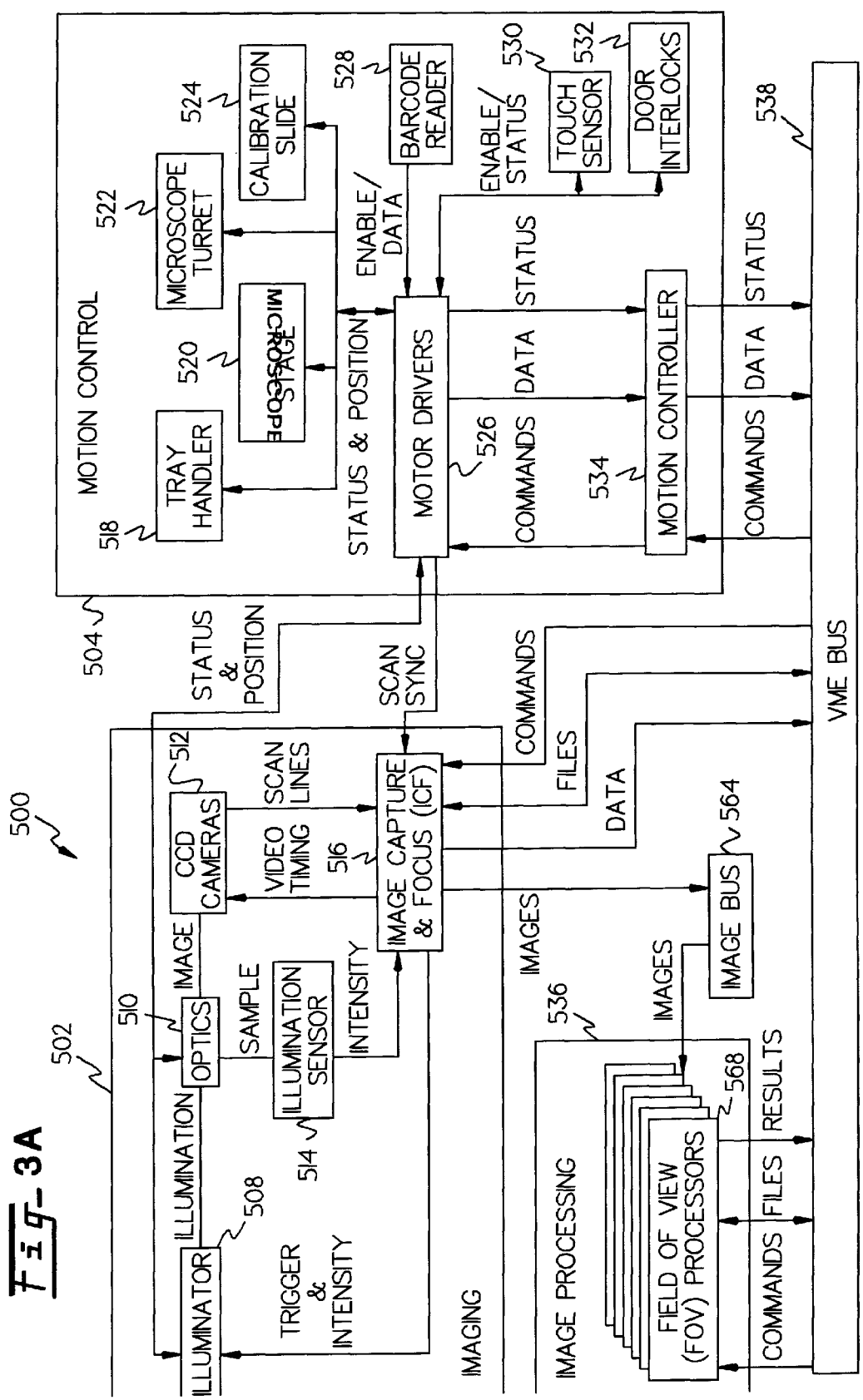

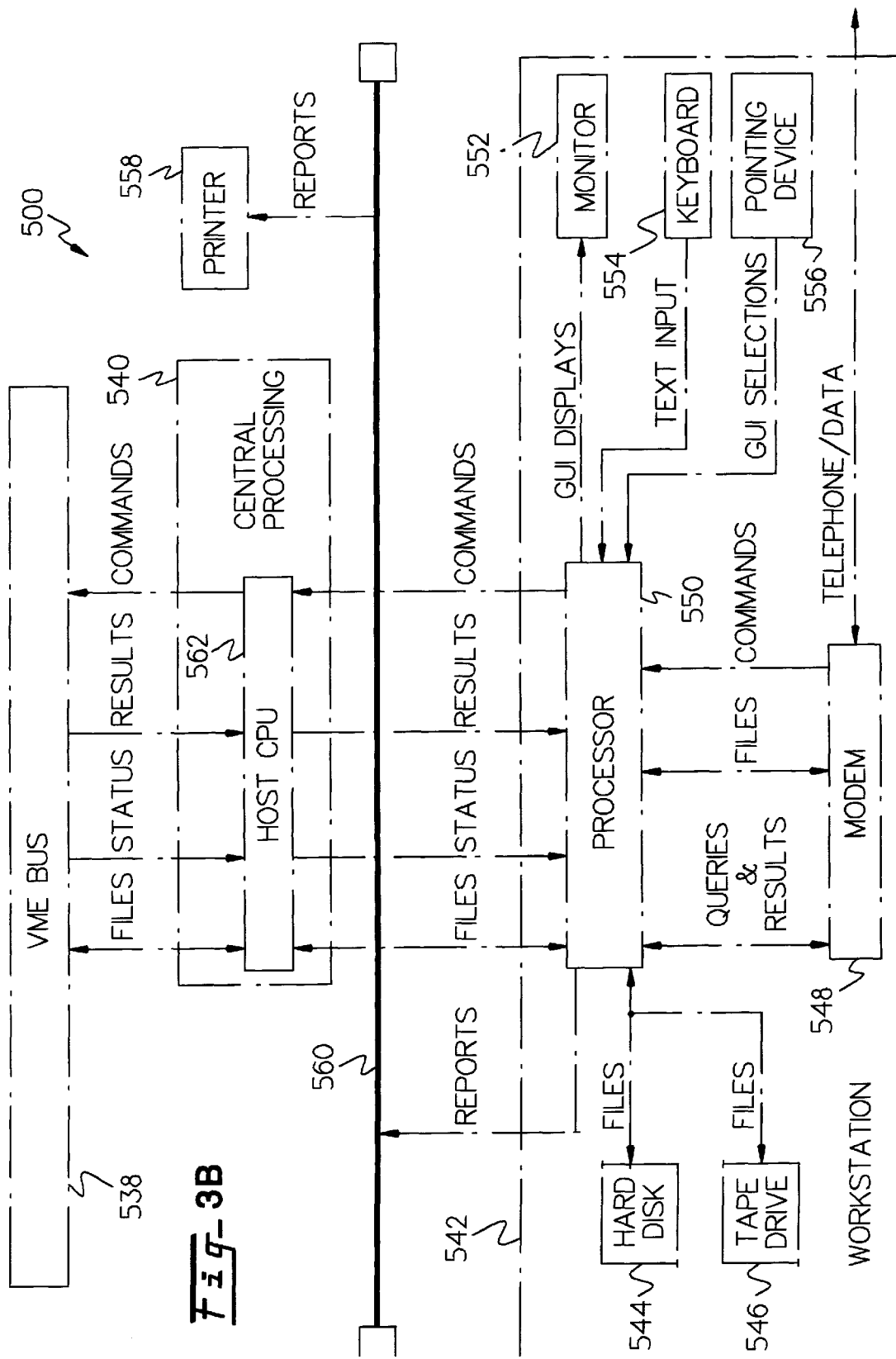

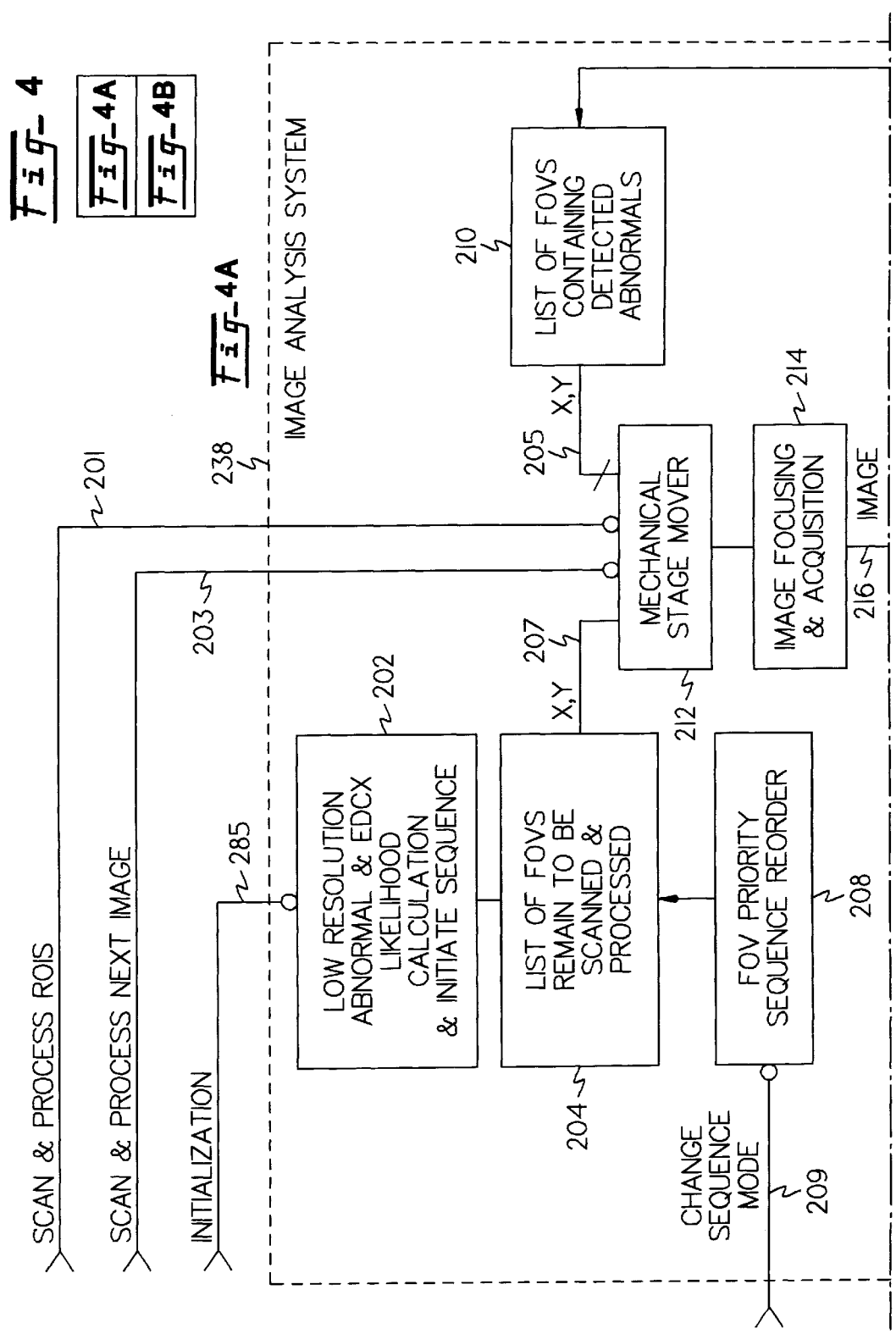

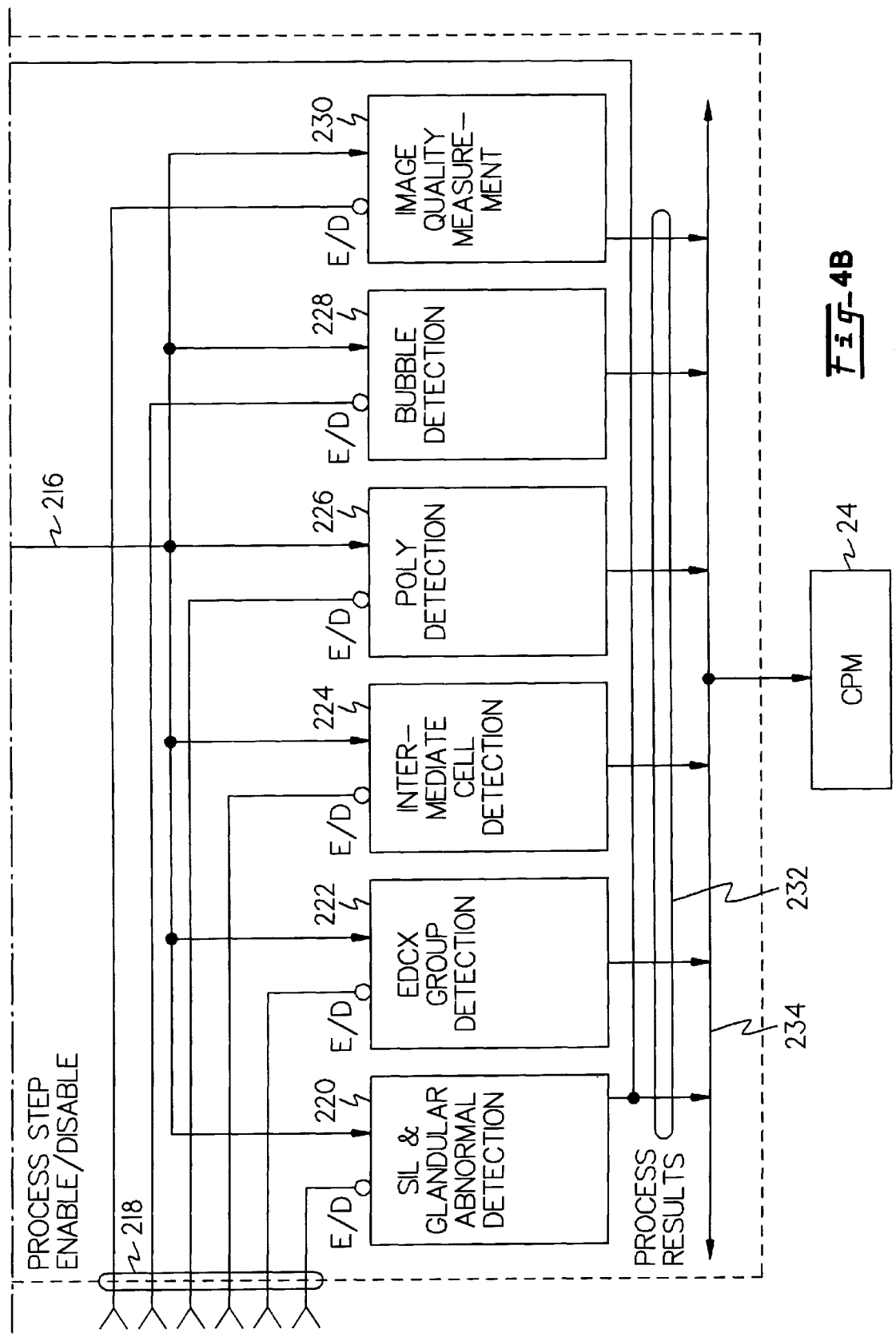

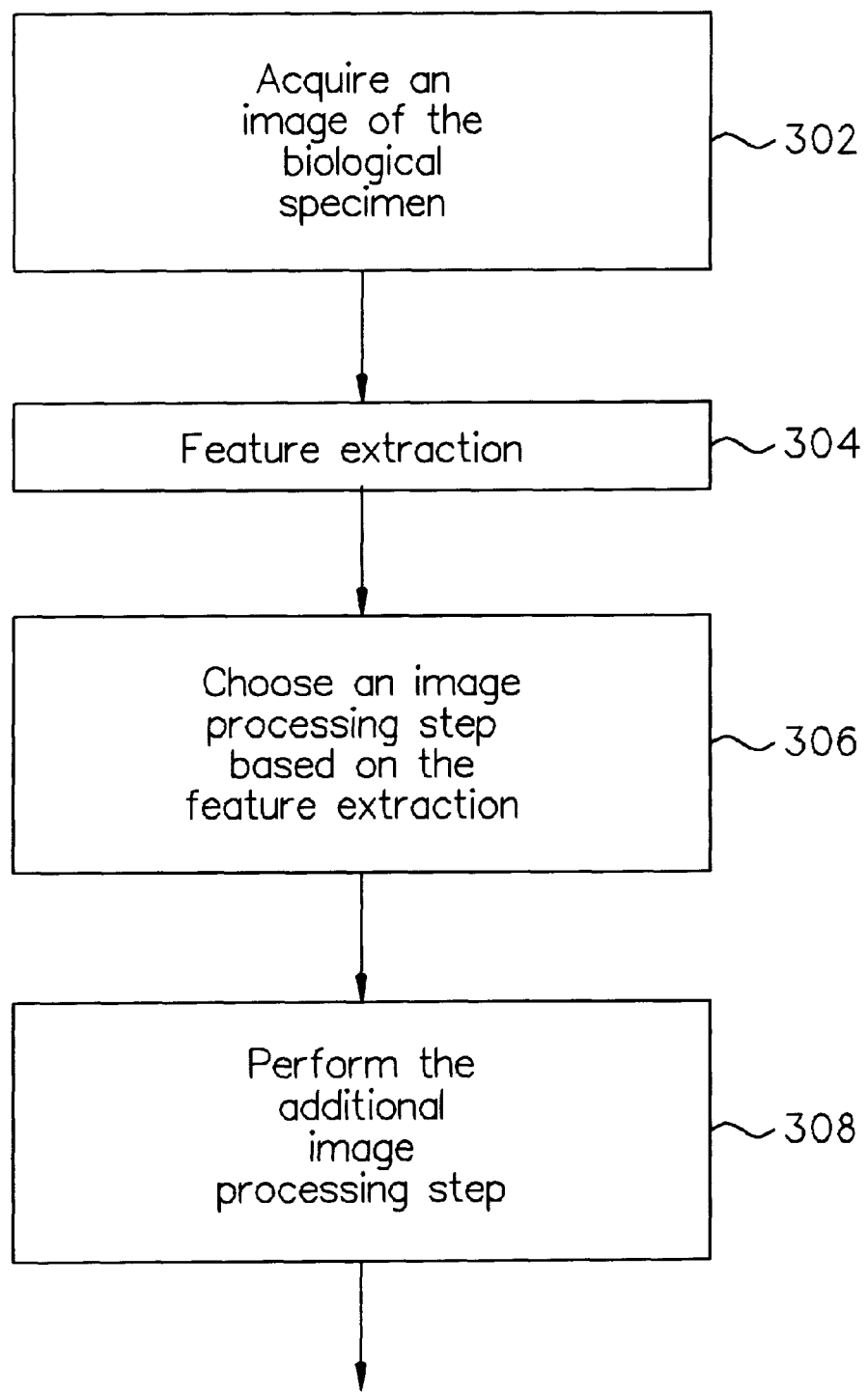
Fig_5

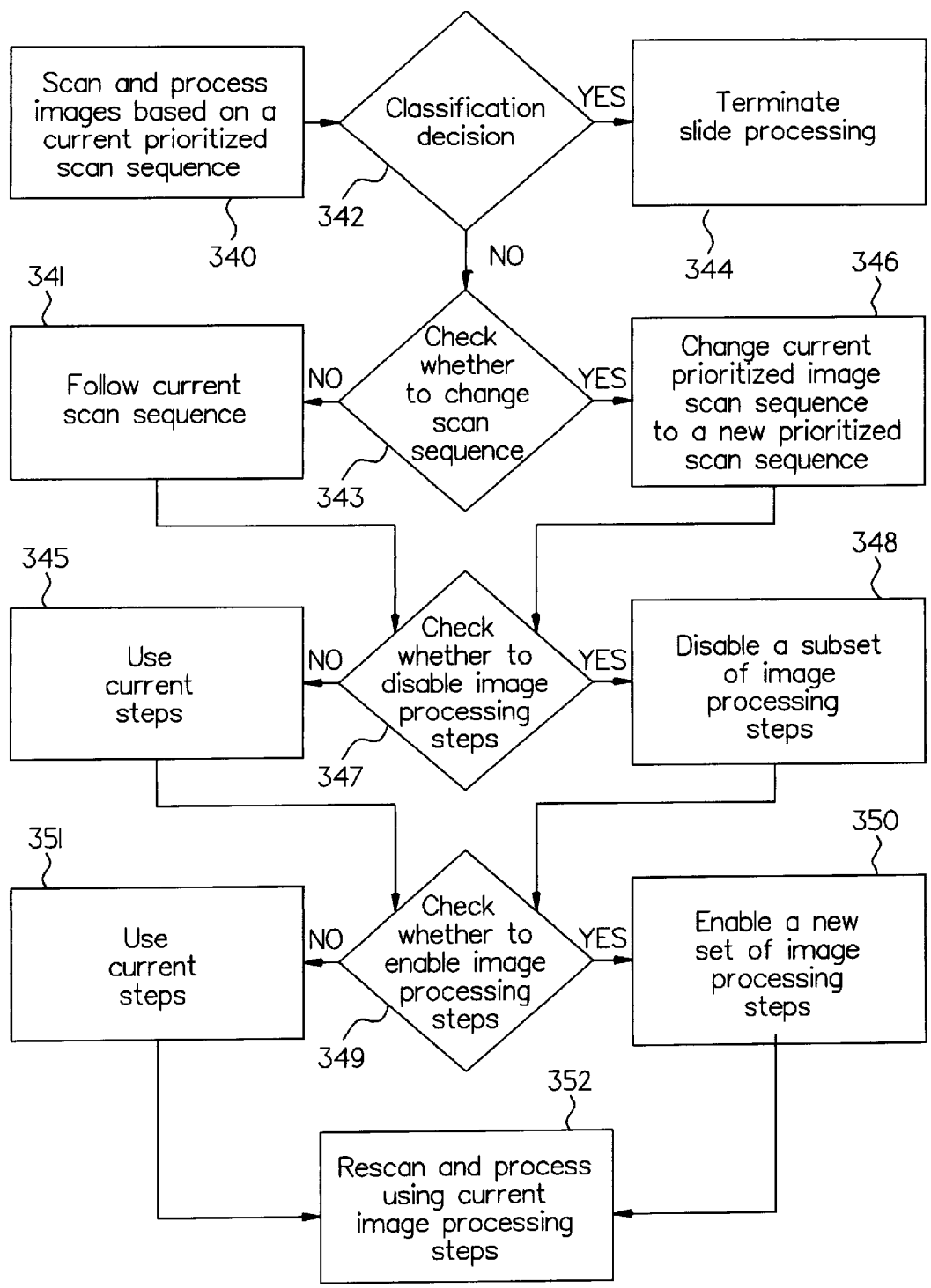
Fig_9

DYNAMIC CONTROL AND DECISION MAKING METHOD AND APPARATUS

METHOD AND APPARATUS

The invention relates to a dynamic control and decision making method and apparatus for an image analyzer and more particularly to a method and apparatus that improves system performance of an automated, image based biological specimen analysis system by increasing processing speed and prescreening accuracy.

BACKGROUND OF THE INVENTION

Systems that process image data at rates acceptable for automated diagnostic prescreening, automated diagnostic screening and automated diagnostic screening quality control include the system disclosed in U.S. Pat. No. 5,315,700, entitled "Method And Apparatus For Rapidly Processing Data Sequences", by Richard S. Johnston et al. issued May 24, 1994 which is incorporated by reference hereto. These systems process images of biological specimen slides such as Pap smear slides. The biological specimen is taken from a patent that is part of a patient population. These systems automatically review the slide and provide an analysis score. The performance of these systems and similar image analysis systems depend on many factors including: the cellular materials composition of the slides to be screened; the speed of the system to scan and process images; the regular patient population composition; the operational mode of the system including system specificity and system sensitivity; and the variations between specimens. The slide processing speed of such systems determines their capacity and thus their operational cost. These systems also have associated signal to noise characteristics. The signal comprises the abnormal cellular material on the processed slides. The noise comprises the artifact or normal cellular material misclassified as abnormal material by these systems. Poor signal to noise characteristics adversely effect the classification effectiveness of these systems.

For example, the task of examining biological specimen slides for the prescreening of cervical cancer demonstrates the need for increasing processing speed and accuracy of automated specimen screeners. Each biological specimen slide exhibits large variability in abnormal cell prevalence. To routinely achieve the high sensitivity required on low-prevalence abnormal specimens, specimens that have a low number of abnormal material, these systems must process a significant number, if not all, of the images taken of the biological specimen slide. Consequently, the number of images these systems must process determines system throughput. In the prior art, the number of images to process is predetermined based on predefined criteria. As a result, the prior art treated each biological specimen slide identically, disregarding data collected from the slide during processing, using a simple sequential test methodology. In some instances this may degrade the signal to noise characteristics of the analysis by including noisy information. The invention recognizes for the first time that an automated analysis achieves optimum signal to noise characteristics during processing. The invention further determines when to stop processing to prevent counterproductive analysis.

Therefore, the invention dynamically processes the biological specimen slide based on data collected from the slide to achieve higher accuracy as well as increased system throughput.

SUMMARY OF THE INVENTION

The invention provides a dynamic decision making method for processing a biological specimen. A computer acquires an image of the biological specimen. The computer processes the image to extract a feature from the image. Using the extracted feature, the computer dynamically chooses additional image processing modules to operate on the image from a predetermined set of image processing modules. The computer may further dynamically adjust the image processing steps performed on the image. The computer then determines whether to acquire a second image and selects the image modules to operate on the second image. The invention thereby provides for enhanced throughput by avoiding unnecessary additional computation.

The invention further provides a dynamic slide classifier for improving system performance of an automated system by increasing processing speed and prescreening accuracy. The dynamic slide classifier includes a means for slide scoring having a process control input and a slide score processing result output; and a means for process control connected to the slide score processing result output, wherein the means for process control is connected to the process control input. In one embodiment, the means for slide scoring further comprises: means for image focusing and acquisition having an image output; means for image processing and feature extraction connected to the image output having a processed image output; and means for processing the processed image output having a control input connected to the process control input. In an alternate embodiment, the means for process control further comprises: means for score calculating connected to the slide score processing result output, wherein the means for score calculating has a review specimen output and a normal specimen output; means for making an automatic inference connected to the slide score processing result output; and means for controlling the means for slide scoring having a control output connected to the process control input.

The invention also provides a method of image scanning and processing comprising the steps of: scanning and processing images based on a current prioritized image scan sequence; terminating slide processing when a classification decision is made; changing the current prioritized image scan sequence to a new prioritized scan sequence; disabling a subset of image processing to reduce unnecessary computation; enabling a new set of image processing to collect new information from the slide; and rescanning and processing certain areas using different image processing.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIGS. 2A and 2B show the method of the invention to dynamically control automated sorting of biological specimens.

FIGS. 3A, 3B and 3C show one embodiment of the invention.

FIGS. 4A and 4B show the method and apparatus of the invention to dynamically control an automated cytology system.

FIG. 5 shows the method of the invention to perform an image processing decision based on the result of an image feature extracted from an image.

FIG. 9 shows the method of the invention to decide whether to rescan and process different areas of the slide using different image processing steps.

DETAILED DESCRIPTION OF THE PREFERRED EMBODIMENT

Figure 1:
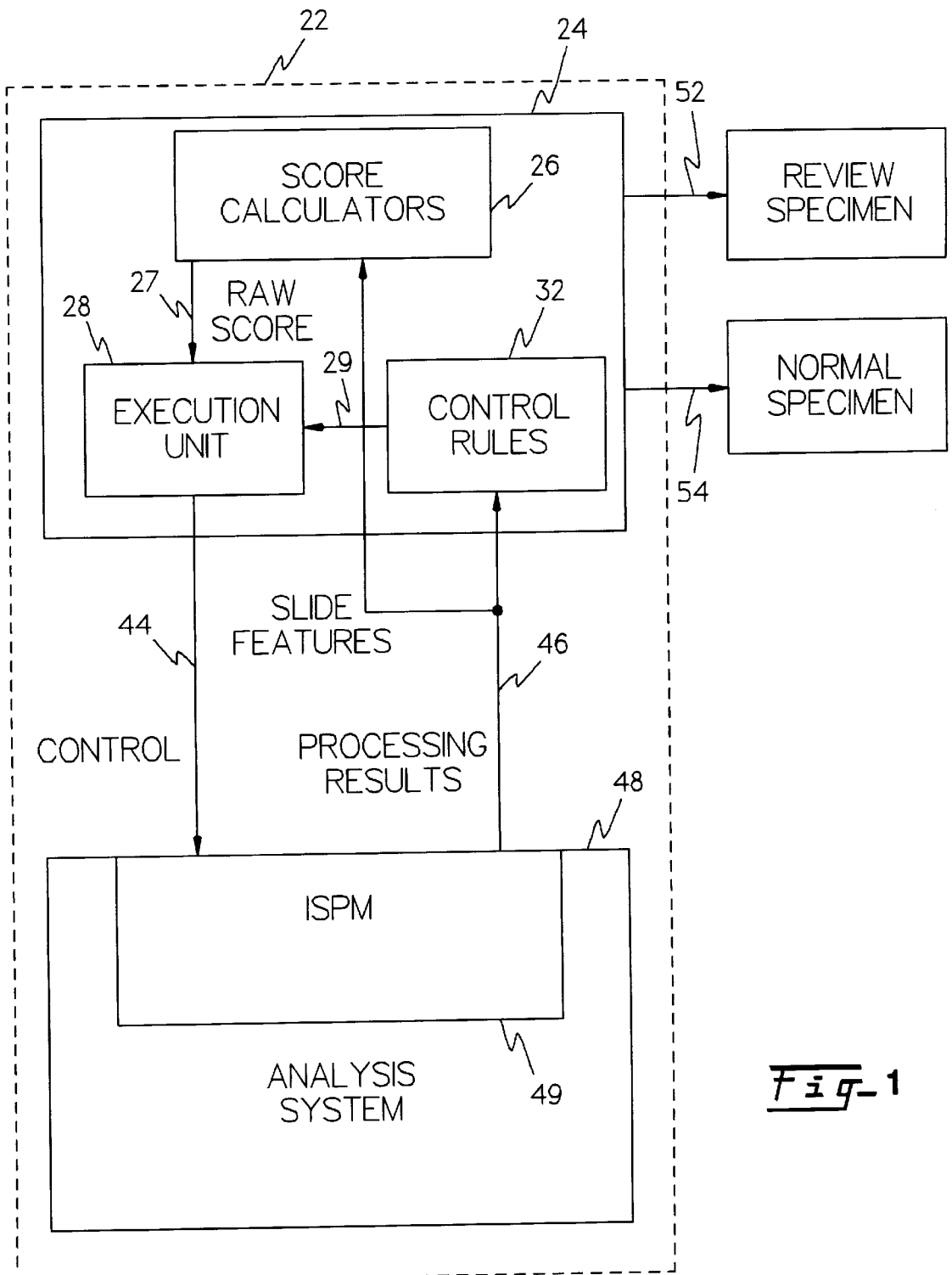
FIG. 1 shows the control process module of the invention in a hardware schematic diagram.
Figure 3C:
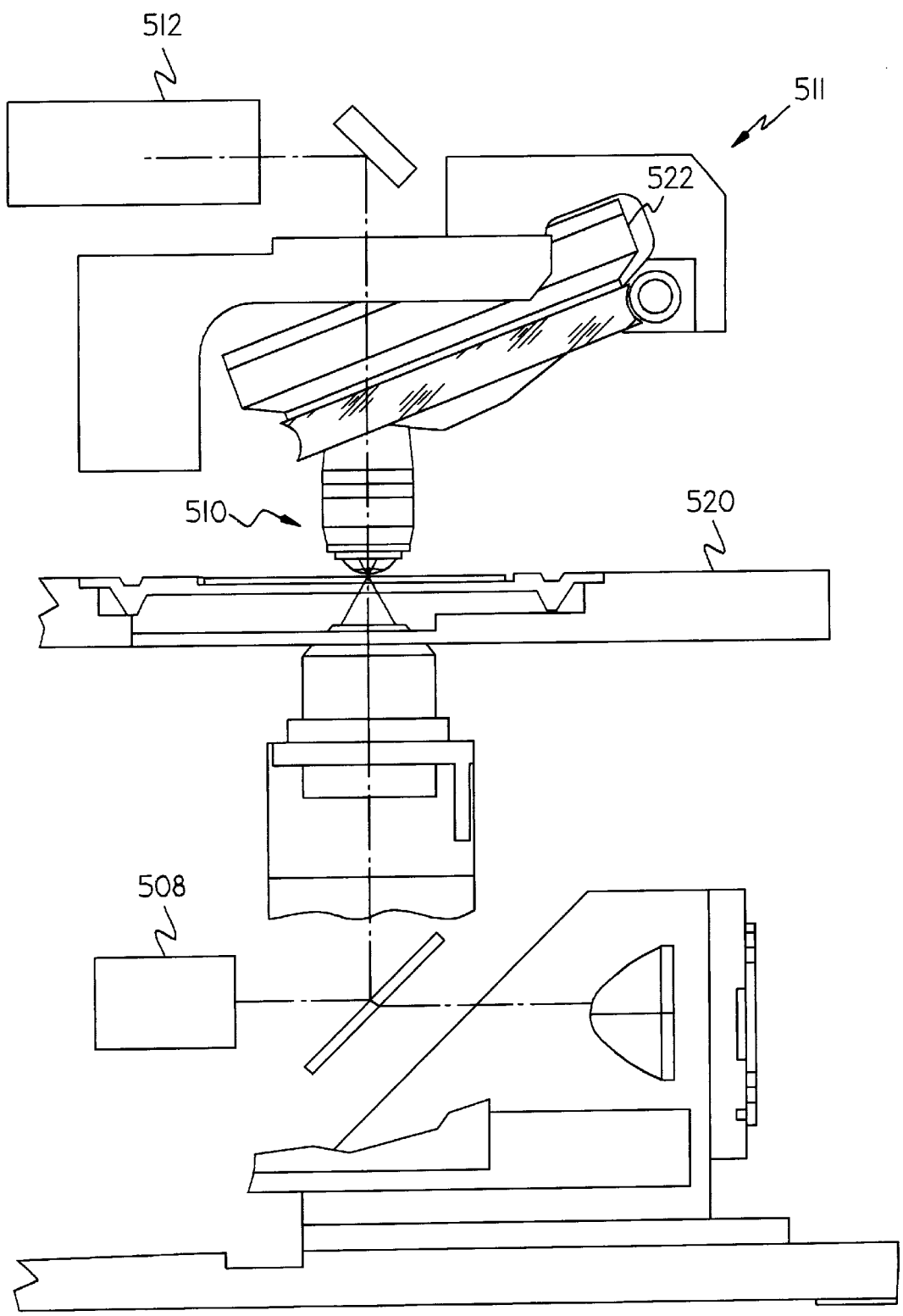

Refer now to FIG. 1 which shows a schematic diagram of the apparatus of the invention. The dynamic decision making system 22 comprises a Control Process Module CPM 24 and an image analysis system 48. The CPM 24 controls the operation of an image analysis system 48. The dynamic decision making system 22 may comprise an image based biological specimen analysis system, an automated diagnostic prescreener, an automated diagnostic screener, or an automated diagnostic screening quality control system. One example embodiment of an image based biological specimen analysis system is shown in FIGS. 3A, 3B and 3C. The CPM 24 controls the image analysis system 48 though control line 44 and receives information from the image analysis system 48 through processing results line 46. The execution unit 28 receives a raw score signal on raw score line 27 from score calculators 26 and a control input 29 from control logic 32 to direct the control of the analysis system 48. The execution unit 28 generates a control signal on control line 44. The control line 44 transmits operational commands to the image analysis system 48 that change the type of processing performed on the image data obtained by the image analysis system 48. In one embodiment of the invention, the image analysis system transmits processing results on processing results line 46. The image scanning and processing module ISPM 49 transmits slide image features to the CPM 24.

The CPM 24 processes the processing results, such as image features, using a data-driven control mechanism. The CPM 24 dynamically controls the image analysis system 48 based on the processing results. CPM 24 employs decision making methods that flexibly determine the image processing modules or steps needed to perform an effective image analysis. For example, in a biological specimen analysis system the dynamic control and decision making method of the invention flexibly determines the processing steps needed to reach a confident classification decision about each biological specimen.

The data-driven control mechanism of the invention improves system accuracy and reduces unnecessary or even counterproductive computation thereby enhancing system throughput, thus increasing the economic value of the system. In addition, by reducing counterproductive computation, the invention tries to maximize the signal to noise characteristics of the system.

There is a point during image processing where further processing becomes counterproductive. The invention finds this processing point. At this point processing is halted and the classification decision is made.

The CPM 24 controls the operation of the image analysis system 48, which in another embodiment of the invention may be an image scanning and processing module, based on data already gathered about the specimen. The CPM 24 monitors the progress of the analysis and interacts with the processing being performed by the image analysis system 48. FIG. 1 illustrates the interactive process connection between image analysis system 48 and the CPM 24.

In one embodiment of the invention, the CPM 24 comprises a set of predetermined control logic driven by an execution unit 28 to determine the actions performed by the image analysis system 48. Those skilled in the art will appreciate that the predetermined control logic may be embodied in software, written in the C programming language for example, running on a CPU such as a general purpose computer, personal computer, or workstation. The execution unit 28 is connected to the image analysis system 48. The execution unit 28 receives processing results from process result line 46 and controls the image analysis engine 48 through control line 44. The execution unit 28, in one embodiment, is an expert system that runs in software on a SUN workstation, personal computer or general purpose computer.

One embodiment of the image analysis system 48 is shown in FIGS. 3A, 3B and 3C. The automatic image focusing and acquisition device 516 coupled with an image processor and feature-extractor 536 implements a set of process steps that use the image processor and feature-extractor 536 to segment the image, calculate features from the segmented objects, and classify them as objects of interest, i.e., abnormal cells, or endocervical component cells. In one embodiment of the invention, image scanning and processing is a sequential process. After i images are scanned and processed, the system reaches the decision point i. At each decision point i of the process, the CPM 24 will do either one or a combination of several of the steps below:

(1) command the image processing system 48 to continue to scan and process more images based on a current prioritized image scan sequence, or (2) command the image processing system 48 to terminate slide processing because the specimen classification decision has been made, or (3) change the current prioritized image scan sequence to a new prioritized scan sequence, or (4) disable a subset of image processing steps in the image processing system 48 to reduce unnecessary computation, or (5) enable a new set of image processing steps in the image processing system 48 to collect new information from the slide, or (6) rescan and process certain areas, such as Regions of Interest ROI's where ambiguous alarms were found, using a different set of processing steps.

For example, as applied to the application of Pap Smear prescreening, the decision of sorting slides as normal or review depends on the detection of adequate endocervical components and squamous cells, and the detection of abnormal cells. A slide will be declared as clearly normal 54 if adequate endocervical components and squamous cells are detected, and no abnormal cells are detected. Otherwise, the slide is sorted out as review 52.

Slide processing starts with the determination of a prioritized scan sequence. The priorities used to create the sequence can be based on, for each subarea of a slide, the evaluated probabilities of containing either endocervical components, or abnormal cells, or both, in each subarea of the slide. Then, the CPM 24 initiates the image analysis system 48 to process the slide following a selected prioritized scan sequence.

According to the control logic 32 the slide processing continues until the CPM 24 reaches a decision of either rejecting the slide for human review or accepting it as a clearly normal slide. According to one embodiment of the invention, certain slide processing steps terminate when sufficient information of a certain type, such as an adequate number of normal endocervical component cells have been detected. In one embodiment, this is a predetermined value based on maximizing the system's sensitivity to slides with endocervical components and with fixed system specificity of slides without endocervical components.

For example, a system may achieve 90% sensitivity with 90% specificity. The subsequent scan sequence will be changed to scan areas having higher probability of abnormality alone. These areas are identified in the initial prioritization scan of the slide. Also, since there is no need to detect more endocervical components, a predetermined subset of image processing steps for the endocervical cell classification are disabled in the ISPM 49. A new set of image processing steps are enabled when certain types of information have been detected, such as an abundance of small objects in the size range of polymorphonucleocytes. The detection of this condition triggers the need to check for certain other conditions on the slide. A set of new processing steps are then activated in the image analysis system 48 to determine whether those conditions such as infections are present or not. The typical new steps are designed to classify small size objects such as polymorphonucleocytes. Areas of the slide are rescanned and reprocessed when inconclusive conditions such as low confidence abnormal cells and alarms are detected on the slide that require further analysis to drive the final slide sorting decision. The areas containing the detected low-confidence alarms will be rescanned, optionally in higher magnification, and analyzed by a different set of processing steps.

In one embodiment of the invention, the CPM 24 employs a dynamic score-thresholding method. In the dynamic score-thresholding method of the invention a rule-based control system such as a simple confidence or score-thresholding method determines the nature of further image processing. The system control process does not dynamically determine what area of a specimen to scan and process by the scanning and processing module, instead, it follows a predetermined ordering before the scan and process sequences begin. The order may reflect the difference of probabilities of different types of abnormality conditions.

In one embodiment of the invention, the image processing system 48 comprises an image scanning and processing module ISPM 49. The ISPM 49 may signal the termination of CPM 24 processing. While processing a specimen, the CPM 24 is continuously, for every FOV processed, receiving processed data from ISPM 49, accumulating the results, and computing a score $S_i$ that reflects the probability of the specimen being abnormal. The score is transmitted to the CPM 24 on processed results line 46. The decision logic in the CPM 24 is based on sets of thresholds that are determined during the system design and training phase.

The score $S_i$, computed by Score Calculator 26 in CPM 24 for each decision point i, comprises part of the input to the control logic for determining whether to terminate slide processing. $S_i$ of decision point i is a computed score reflecting the probability of a specimen being abnormal. Each score $S_i$ is computed based on the accumulated information from the beginning of the slide processing up to the decision point i. At each i, a set of slide features $F_{i1} \ldots F_{in}$ are computed. Each slide feature $F_{ik}$ is an accumulated algorithm processing output or a derivation from it. $F_{ik}$ are accumulated and derived by score calculator 26, such as the accumulated number of cells classified as abnormal, and their average integrated optical density. The scoring functions $G_i$ can be any statistical classification method, such as decision tree, linear or non-linear mapping function, that applies combined high-dimensional slide features to generate a numeric value. In one embodiment, $G_i$ are Fisher's linear discriminant function. The features, as well as the scoring function $G_i$ used to compute each $S_i$, could be different for each i.

$$S_i = G_i(F)$$
$$= G_i(F_{11}, F_{12}, \cdots F_{il}, F_{21}, F_{2n}, \cdots F_{in})$$

The candidate feature set $F_i$ for computing $S_i$ comprises all accumulated slide features at all decision points j, $1<=j<=i$. That is, $F=[F_{jk}, 1<=j<=i, 1<=k<=n]$. A certain subset of features at each j, $j<=i$, may be chosen for computing $S_i$ because different features at different j, $j<=i$, may provide the best discriminating power for each type of abnormality found in the regular patient population. The use of two dimensional (2-D) features has the advantage of providing more discriminating power to separate the abnormal from the normal population. This is because the abnormal cell prevalence of different types of cells, such as squamous SIL, glandular atypical cells, etc., of abnormal slides varies. The false-positive alarm rate of each difference detection process step also varies. Each $F_{jk}$ contributes to discriminating different types of abnormal slides from normal slides. As a result, the discriminating power of different features, e.g., the number of classified abnormal squamous and glandular abnormal cells, can be optimal, in terms of signal to noise ratio, at different control points. This arises because only a limited number of certain types of abnormal cells, the signal, exist on each slide. The images acquired from these specimens were prioritized in terms of the probability of containing these type of cells. Thus, statistically, the signal to noise ratio actually deteriorates if more than the optimal number of images have been processed.

|  |  | 2-D Slide Features |  |  |
|---|---|---|---|---|
|  | 1 | $F_{11}, F_{12}, F_{13}$ | ... | $F_{in}$ |
|  | 2 | $F_{21}, F_{22}$ |  | ... $F_{21}$ |
| Control | 3 | : |  |  |
| Point | : | : |  |  |
|  | i | $F_{il}, F_{12},$ |  | ... $F_{1n}$ |
|  |  | 1 |  | n |

The method and apparatus of the invention departs from the simple sequential random sampling methods of the prior art that assumes uniform probability and use.

Each feature set $G_i$ is determined based on the training data, slide population, collected up to decision point i. The criteria for designing $G_i$ is to optimize the decision so as to reject or accept slides as soon as possible and to obtain a best classification accuracy.

To dynamically sort out a biological specimen as requiring further human review or to indicate that no human review should be done is based on $S_i$. There may be two sets of decision thresholds. One decision threshold set for the early rejection of the slides for human review: $TR_i$ for each decision point i. A second decision threshold set for the early acceptance of the slides as clearly normal, where no review is required: $TA_i$ for each decision point i.

By way of example and not limitation, in the application of prescreening cervical smears such as Pap smears for the detection of precursors and cancerous conditions, a prescreening system usually operates in a high sensitivity mode, which means a significant portion of normal specimens could be selected for human review resulting in a high ratio of false-positives. These false-positives may be the result of various conditions such as improper staining, inflammation, atrophic pattern, and the like. The system may not be able to dismiss the slides as normal no matter how many more images are sampled and processed. Since these false-positive slides require human review, rejecting them as early as possible saves unnecessary processing time and improves the system's overall throughput. A set of early rejection thresholds are used for this purpose. Whenever the score of a slide exceeds the early rejection threshold of that decision point ($TR_i < S_i$), the CPM 24 will ask the ISPM 49 to terminate, and the specimen is selected for human review.

The early acceptance thresholds are used to accept clearly normal slides as no review. For cervical cancer prescreening this condition occurs when a sufficient number of images that have the highest likelihood of being abnormal among the specimen have been sampled and no evidence of abnormality is detected. That is, if the score of decision point i, $S_i$ is less than threshold $TA_i$, then CPM 24 will ask ISPM 48 to terminate. The specimen is then sorted out as normal.

At any decision point i during processing, if neither condition is satisfied, i.e., $TR_i > S_i > TA_i$, processing will continue until the slide is either rejected for review or accepted as clearly normal at a later decision point.

The $TR_i$ at each decision point i is designed to reject as many slides as possible requiring human review based on, for example, a fixed-1,000 image method, with the constraint of not rejecting the acceptable normal slides. The $TA_i$ is chosen to maximize the number of acceptable normal slides with the constraint of not falsely accepting the rejectable abnormal slides. While processing a specimen, as more images are scanned and processed, the computed score will gradually converge. Therefore, the difference between $TR_i$ and $TA_i$ gradually converges to 0.

As an example, the invention was tested at NeoPath, Inc., Redmond, Wash., where the invention effectively worked on a prescreening system that can sort out at least 50% of the normal population as no review and improved system throughput at least 20%. The test was based on a set of 4,543 slides. Each slide is sampled and processed up to 1,000 high-resolution images. While the images are scanned and processed, there is a slide score $S_i$, $0 <= S_i <= 1$, computed at each decision point i, $1 <= i <= 10$. A decision point i may be defined that corresponds to the point where 100×i images have been processed. An example set of $TR_i$ and $TA_i$ are defined as follows:

| Decision Point | $TR_i$ | $TA_i$ |
|---|---|---|
| 1 | 1.0 | 0.0 |
| 2 | 1.0 | 0.0 |
| 3 | 0.3 | 0.0 |
| 4 | 0.3 | 0.0 |
| 5 | 0.3 | 0.0 |
| 6 | 0.3 | 0.0 |
| 7 | 0.3 | 0.085 |
| 8 | 0.28 | 0.095 |
| 9 | 0.2 | 0.099 |
| 10 | 0.1645 | 0.1645 |

The specimen diagnostic distribution is defined based on the regular patient population as follows for the purpose of performance estimation:

| Diagnostic Category | Percentage |
|---|---|
| normal with edcx | 85.5% |
| normal without edcx | 9.5% |
| ASCUS/AGUS | 3.9% |
| LSIL | 0.8% |
| HSIL+ | 0.3% |

The following chart shows the percentage of slides of each diagnostic category that are either rejected or accepted at each decision point. The accumulated results in terms of total rejection and acceptance rates is equivalent to only making the rejection/acceptance decision at the decision point 10, after having processed 1,000 images.

| diag | N w/ edcx | N w/ edcx | N w/o edcx | N w/o edcx | ASCUS /AGUS | ASCUS /AGUS | LSIL | LSIL | HSIL+ | HSIL+ |
|---|---|---|---|---|---|---|---|---|---|---|
| decision point | rejected | accepted | rejected | accepted | rejected | accepted | rejected | accepted | rejected | accepted |
| 1 | 0 | 0 | 0 | 0 | 0 | 0 | 0 | 0 | 0 | 0 |
| 2 | 0 | 0 | 0 | 0 | 0 | 0 | 0 | 0 | 0 | 0 |
| 3 | 10.32 | 0 | 10.15 | 0 | 34.36 | 0 | 50.21 | 0 | 66.85 | 0 |
| 4 | 4.20 | 0 | 2.97 | 0 | 6.13 | 0 | 11.08 | 0 | 7.74 | 0 |
| 5 | 3.24 | 0 | 2.77 | 0 | 6.13 | 0 | 6.00 | 0 | 6.54 | 0 |
| 6 | 3.32 | 0 | 3.18 | 0 | 6.44 | 0 | 4.87 | 0 | 3.71 | 0 |
| 7 | 3.24 | 7.74 | 2.46 | 11.90 | 5.52 | 2.15 | 4.04 | 0.83 | 1.86 | 0.65 |
| 8 | 4.94 | 8.70 | 3.69 | 8.21 | 6.75 | 2.15 | 3.11 | 1.04 | 2.94 | 0.76 |
| 9 | 10.54 | 3.05 | 11.08 | 2.56 | 11.66 | 0.92 | 7.56 | 0.52 | 3.49 | 0.11 |
| 10 | 10.39 | 30.29 | 7.08 | 33.95 | 6.44 | 11.35 | 4.66 | 6.11 | 2.51 | 2.83 |
| Total | 50.22 | 49.78 | 43.38 | 56.62 | 83.43 | 16.57 | 91.50 | 8.50 | 95.65 | 4.35 |

For accuracy comparison, the following table lists the system performance of processing 1,000 fixed images per slide:

| diag | N w/ edcx | N w/ edcx | N w/o edcx | N w/o edcx | ASCUS /AGUS | ASCUS /AGUS | LSIL | LSIL | HSIL+ | HSIL+ |
|---|---|---|---|---|---|---|---|---|---|---|
| By 1000 images | rejected | accepted | rejected | accepted | rejected | accepted | rejected | accepted | rejected | accepted |
| Total | 50.12 | 49.88 | 43.90 | 56.10 | 82.82 | 17.18 | 91.41 | 8.59 | 95.65 | 4.37 |

Note that on average, slides rejected at decision point 3, 4, etc use only 30%, 40% . . . of the computation time for processing 1,000 images respectively. Therefore in total, early rejection mechanisms can save 15.7% of the computation time for normal with edcx slides, 14.1% for normal without edcx slides, 37.5% for ASCUS/AGUS slides, 49.3% for LSIL slides, and 57.7% for HSIL+slides. By using the regular patient population diagnosis distribution shown above to do the improvement projection, the early rejection mechanism can save up to 16.8% of the computation time. Similarly, the early acceptance mechanism can save 4.4% of the computation for N with edcx, 5.5% for N without edcx, 1.2% for ASCUS/AGUS slides, and 0.5% for LSIL slides. The total saving by early acceptance mechanism is 4.3% for the regular patient population.

The above estimation sums up to a total of 21.1% of computation saving by this score-thresholding based dynamic control and decision making DCDM mechanism, yet achieves the same level of accuracy as a system that processes 1,000 images for every slide.

The above example uses 1,000 as the maximum number of images to process per slide. To improve screener system sensitivity and accuracy, the number may be extended. That is, slides that can not be sorted out as either rejected or accepted will go on to scan and process more images as required. This dynamic method can help those abnormal slides that have low prevalence of abnormal material. Because this extended computation requirement only occurs for a small portion of the slides that are not sorted out yet, the impact on average slide processing time will be limited.

Refer now to FIG. 5 which shows the method of the invention to perform an image processing decision based on the result of an image feature extracted from the image. The image processing decision involves determining whether or not to perform an additional image processing module or step on the image. The process starts at step 302, where the method of the invention acquires an image of the biological specimen. As stated herein, the biological specimen can be, for example, a Pap smear. In step 304, the method of the invention performs feature extraction to extract features from the image of the biological specimen. In step 306, the method of the invention chooses an image processing module, step or steps based on the feature extraction step 304. Depending on the type of feature extracted in step 304, a variety of processing modules will be executed. These image processing modules include: SIL, Edcx, intermediate cell, poly, bubble, image quality measurements and other image processing and object detection steps as described herein. The method of the invention now flows to step 308 to perform the additional image processing modules or steps.

Figure 2B:
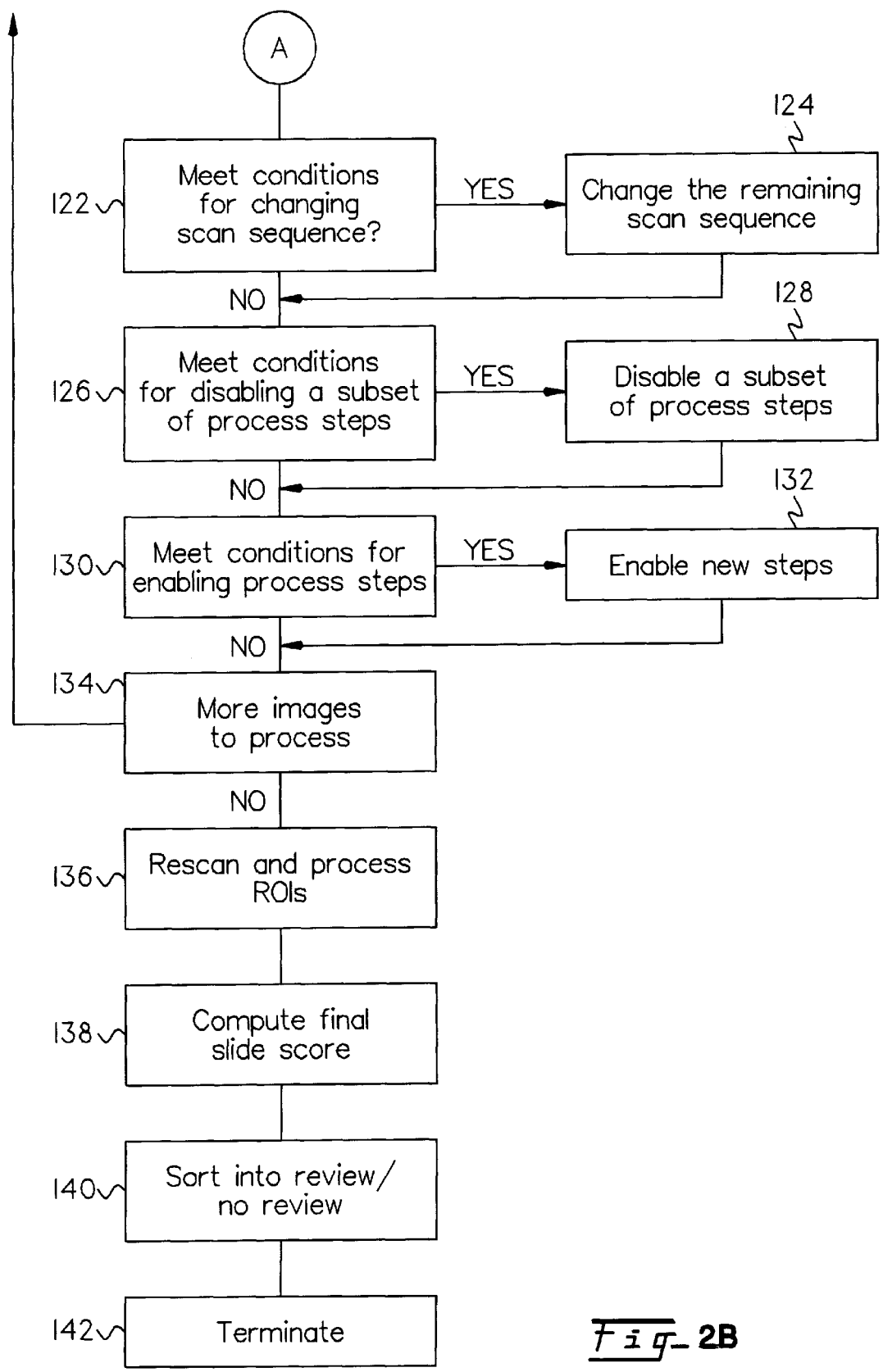

FIGS. 2A and 2B show the method of the invention to dynamically control the sorting of biological specimens. In process block 102, slide processing starts on an automated biological slide sorting apparatus. In one embodiment of the invention, slide processing is intended to sort the specimen into two categories; either not needing human review or needing human review. Those skilled in the art will appreciate that other slide processing procedures and slide sorting methods may benefit from the method of the invention.

Figure 2C:
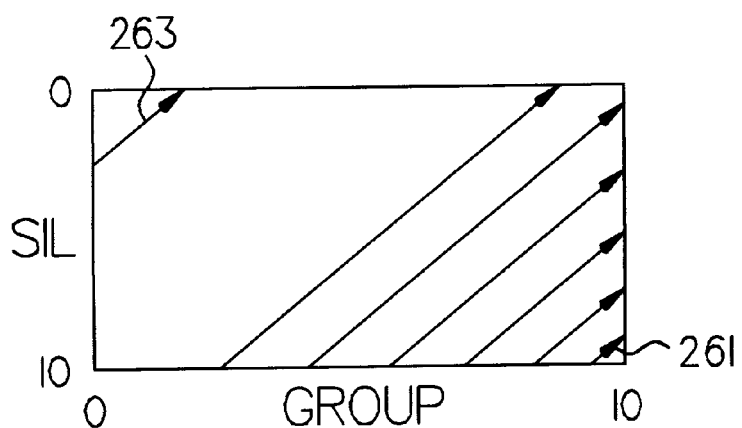
FIGS. 2C, 2D and 2E show the scan sequences of the invention.

In process step 104, an initial prioritized scan sequence is determined and an initial set of processing steps are chosen to analyze the biological slide. The biological slide scans are prioritized according to a predetermined criteria. A low resolution scan determines the prioritized scan sequence based on the likelihoods of containing abnormals and endocervical cell groups in each image. The sequence is initialized as a balanced sequence as shown in FIG. 2C. For each field of view the classifier will determine a Group score and a SIL score, shown on the x axis and y axis respectively. The group score indicates the likelihood of containing endocervical cell groups, Edcx, and the SIL score indicates the likelihood of containing abnormal cells. On the x axis, the group score is plotted from zero to ten where ten indicates that the field of view most likely contains a group. On the y axis, the SIL score is plotted from zero to ten where ten indicates that the field of view most likely contains an abnormal cell. The balanced scan sequence of FIG. 2C indicates that those fields of view that have a high group score and a high sil score are looked at first, as indicated by scan 261. Those fields of view that have both a low SIL score and a low group score are looked at last, as indicated by scan 263.

The following processes are initialized in the ISPM 49:
SIL: for detecting abnormal squamous or glandular cells, and intermediate cells; and
GRP: for detecting normal Edcx cell groups.

In process block 106 each scan image is processed in sequence. In step 108, a decision point is reached as to whether or not to continue computing slide features. If the number of images processed $N>=t1$ and n mode $x=0$, then N is a decision point, where t1 and x are predetermined constants. If slide features are to be processed, the method of the invention continues to step 112 to compute the 2D slide features. The 2D slide features are computed from all i images, $t1<=i<=n$. If slide features are not to be further processed the method of the invention steps to process step 120.

In step 114, the slide score $S_i$ is computed. In step 116, a classification decision is reached based on the slide score. The decision reached is based on the Score $S_i$:
if $(S_i>=R_i)$ then review;
if $(S_i<N_i$ and # edcx group detected $>Et$) then no review;
else no decision can be made yet; where $R_i$, $N_i$ and Et are predetermined thresholds.

Figure 2D:
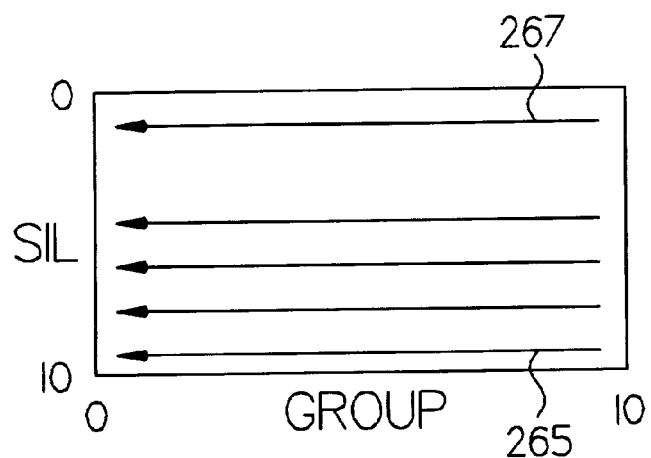
Figure 2E:
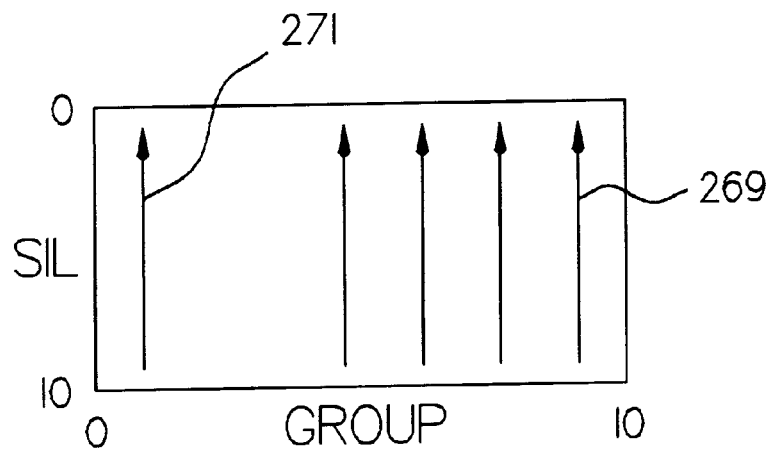

If a classification decision is made, the slide is sorted into review or no review at step 118. If a decision is not reached on the score, the process flows to step 122 to determine if properties of the scan meet conditions for changing the scan sequence. If the properties of the scan meet these conditions, the remaining scan sequence is changed in step 124. The scan sequence is changed if the number of endocervical groups detected is greater than $Z_r$. If so, the sequence is changed to abnormal-cell major shown in FIG. 2D. Fields of view with high SIL scores, shown by scan 265, are checked first in order of group score. Fields of view with low SIL scores, shown by scan 267, are checked last in order of group score. If the number of suspicious abnormal cells detected is greater than At, then the sequence is changed to Edcx-group major shown in FIG. 2E, where $Z_t$, At are predetermined thresholds. Fields of view with high group scores, shown by scan 269, are checked first in order of SIL score. Fields of view with low group scores, shown by scan 271, are checked last in order of SIL score. Those skilled in the art will recognize that slide classification decisions based on other criteria and methods, other than slide scores, are within the spirit and scope of the invention.

In step 126, the process checks to see if the result of scanning the specimen meets conditions for disabling a subset of processing steps. If the specimen does, the subset of processing steps are disabled in step 128. If the number of endocervical groups detected is greater then $Z_t$ then the group detection process in the ISPM 49 is disabled. If the number of suspicious abnormal cells detected is greater than At, then the SIL detection process in the ISPM 49 is disabled. If the number of detected intermediate cells, for reference, is greater than $I_t$, then the intermediate cell processing in ISPM 49 is disabled.

In step 130, the method of the invention checks to see if conditions for enabling new processing steps are met. If the average number of detected small objects per image are greater than $O_t$ and i>t2, the number of images processed, then the inflammatory condition classifier steps are enabled in ISPM 49, where t2 is a predetermined threshold. If the number of pixels in an image are saturated where the pixel value is equal to or greater than a maximum $M_t$, then the air-bubble detection process is enabled in ISPM 49, where $M_t$ is a predetermined threshold. If dark cell clumps are detected by segmentation, then the thick abnormal cell group classification process is enabled in the ISPM 49. If any of the conditions are met, the method of the invention enables these processing steps in step 132.

In step 134, a check is made to determine if additional slide images remain in the scan sequence and are to be processed. If so, the method of the invention returns to step 106 to process the next slide image. The process then flows to step 136 to rescan and continue processing. If there are no more images available to scan and process, then the specimen can not yet be classified. The specimen is then rescanned and regions of interest are processed that contain detected potential abnormal cells. In step 138 the method of the invention computes the final slide score Si based on the slide feature information extracted from step 136. The invention then sorts the slide for review or no review in step 140 and terminates in step 142 having potentially avoided unnecessary processing.

Figure 7:
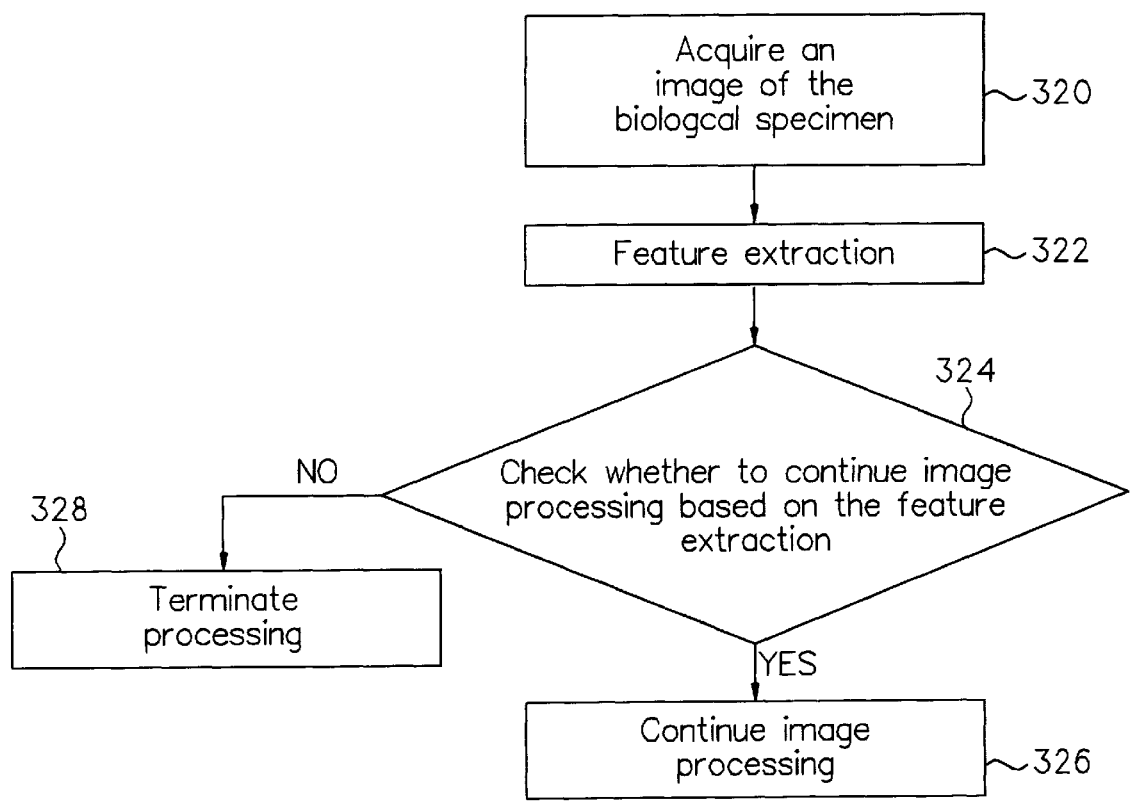
FIG. 7 shows the method of the invention to decide whether or not to continue image processing or perform an additional image processing step.

Refer now to FIG. 7 which shows the method of the invention to decide whether or not to continue image processing or perform an additional image processing step. The method starts in step 320 by acquiring an image of the biological specimen. In step 322, a feature is extracted from the image. In step 324, a check is made as to whether or not to continue image processing following the methods described herein. If the processing should continue, the process flows to step 326 to continue processing. Otherwise the method of the invention terminates image processing in step 328.

Figure 8:
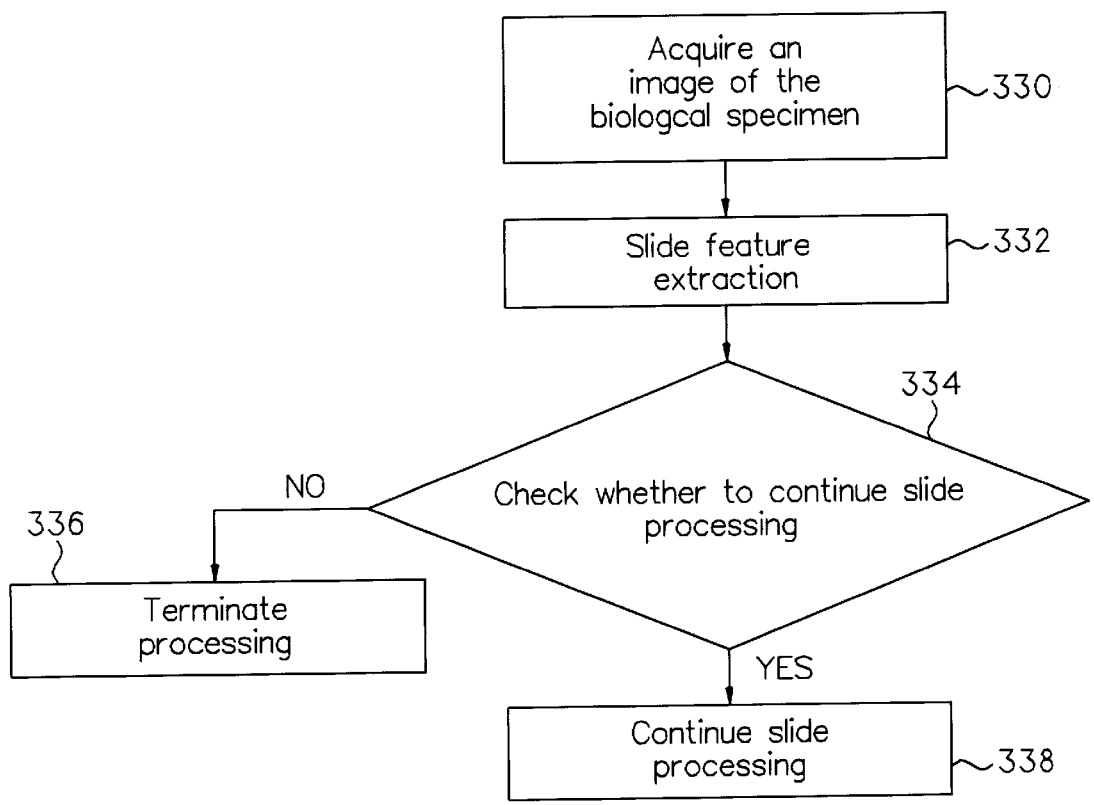
FIG. 8 shows the method of the invention to decide whether to continue slide processing or perform an additional slide processing step.

Refer now to FIG. 8, which shows the method of the invention to decide whether to continue slide processing or perform an additional slide processing step. Slide processing is to be distinguished from image processing by the consideration of information from multiple images of the slide and from slide level information. For example, slide level decisions include whether to keep acquiring additional images from the slide, whether to change the type of images being acquired, or to change the steps used to process the images as described herein. The method of the invention starts in step 330 by acquiring an image of the biological specimen. In step 332, a slide feature is extracted from the image. In step 334, a check is made as to whether or not to continue slide processing following the methods described herein. If the slide processing is to continue, the process flows to step 338 to continue slide processing. If, in step 334, the method of the invention decides not to continue slide processing, the process flows to step 336 to terminates slide processing.

Now refer to FIGS. 4A and 4B which show an alternate embodiment of the invention to dynamically control processing in an automated cytology analysis system. In one embodiment of the invention, the image analysis system 238 receives three control signals: the scan and process enable signal 201, the scan and process next image signal 203 and the initialization signal 285. The scan and process enable signal 201 and scan and process next image signal 203 are provided to the mechanical stage controller 212. The mechanical stage controller also receives the x, y stage control signals 207, 205 from the list of field of views that remain to be scanned and processed 204 or the list of field of views that contain detected and abnormal cells 210.

The initialization signal 285 is provided to the initial sequencer 202 that performs a low-resolution abnormal and Edcx likelihood calculation and generates a sequence of field of views to scan. The calculation determines which fields of view that are most likely to contain abnormal and Edcx cells. A list of field of views that remain to be scanned 204 are output from the initial sequencer 202. A field of view priority sequence reorder is done by a processor 208. FOV priority sequence reorderer 208 changes the FOV priority sequence in response to change sequence mode control line 209. In one embodiment, the processor 208 can be a microprocessor. Processor 208 reorders the field of views based on a selected criteria, such as the method described in assignee's U.S. Pat. No. 5,757,954, issued May 26, 1998 to Kuan et al., entitled "Field Prioritization Apparatus and Method". The microscope stage is moved by mechanical stage controller 212 to the x, y position of the field of view. The image focusing and image acquisition system 214 provides an image 216 of the field of view. This image is then provided to a number of sub processors that perform a range of image processing tasks. The control process module, CPM 24, enables or disables each of these subprocesses by control line 218. Each sub process provides processing results 232 to the control process module on results output 234.

In the Sil and glandular abnormal detection subprocess 220, the image 216 is processed to detect abnormal cells that are likely to be Sil and glandular abnormal. This processing is described in more detail in applicant's U.S. Pat. No. 5,978,497, issued Nov. 2, 1999, to Lee et al., entitled "APPARATUS FOR THE IDENTIFICATION OF FREE-LYING CELLS"; U.S. Pat. No. 5,978,498, issued Nov. 2, 1999 to Wilhelm et al., entitled "APPARATUS FOR AUTOMATED IDENTIFIC ATION OF CELL GROUPINGS ON A BIOLOGICAL SPECIMEN" which is a file wrapper continuation of abandoned U.S. patent application Ser. No. 08/309,061; and U.S. Pat. No. 5,987,158, issued Nov. 16, 1999 to Meyer et al. Entitled "APPARATUS FOR AUTOMATED IDENTIFICATION OF THICK CELL GROUPINGS ON A BIOLOGICAL SPECIMEN" which is a file wrapper continuation of abandoned U.S. patent application Ser. No. 08/309,116.

In the Edcx group detection subprocess 222, the image 216 is processed to detect Edcx groups. This processing is also described in more detail in the above referenced applications.

In the intermediate cell detection subprocess 224, the image 216 is processed to detect intermediate cells. The processing is also described in more detail in the above referenced applications.

In the poly detection subprocess 226, the image 216 is processed to detect poly cells. This processing is also described in more detail in the above referenced applications.

In the bubble detection subprocess 228, the image 216 is processed to detect bubbles in the coverslip adhesive. This processing is described in more detail in applicant's U.S. Pat. No. 5,566,249, issued Oct. 15, 1996 to Rosenlof et al., entitled "APPARATUS FOR DETECTING BUBBLES IN COVERSLIP ADHESIVE".

In the image quality measurement subprocess 230, the image is processed to measure the image's quality. If the image is saturated, then there may be an air bubble.

Those skilled in the art will recognize that the invention can control other image processing operations other than the ones shown. By avoiding various subprocessing steps the time required to analyze and rescan the fields of view is reduced.

The invention generates another list of fields of view that contain detected abnormal cells 210. This list is used as an input to the mechanical stage mover 212. The image analysis system proceeds to rescan each one of these fields of view.

The results output 234 contains information about the field of view such as the number of objects that are squamous, glandular or a member of a cell group, the number of cells detected that have a likelihood of abnormality and the associated confidence of the likelihood, the number of normal intermediate cells detected, the features of the normal cells detected, the number of squamous cells detected, the number of small objects detected and the number of pixels that are saturated.

Figure 6:
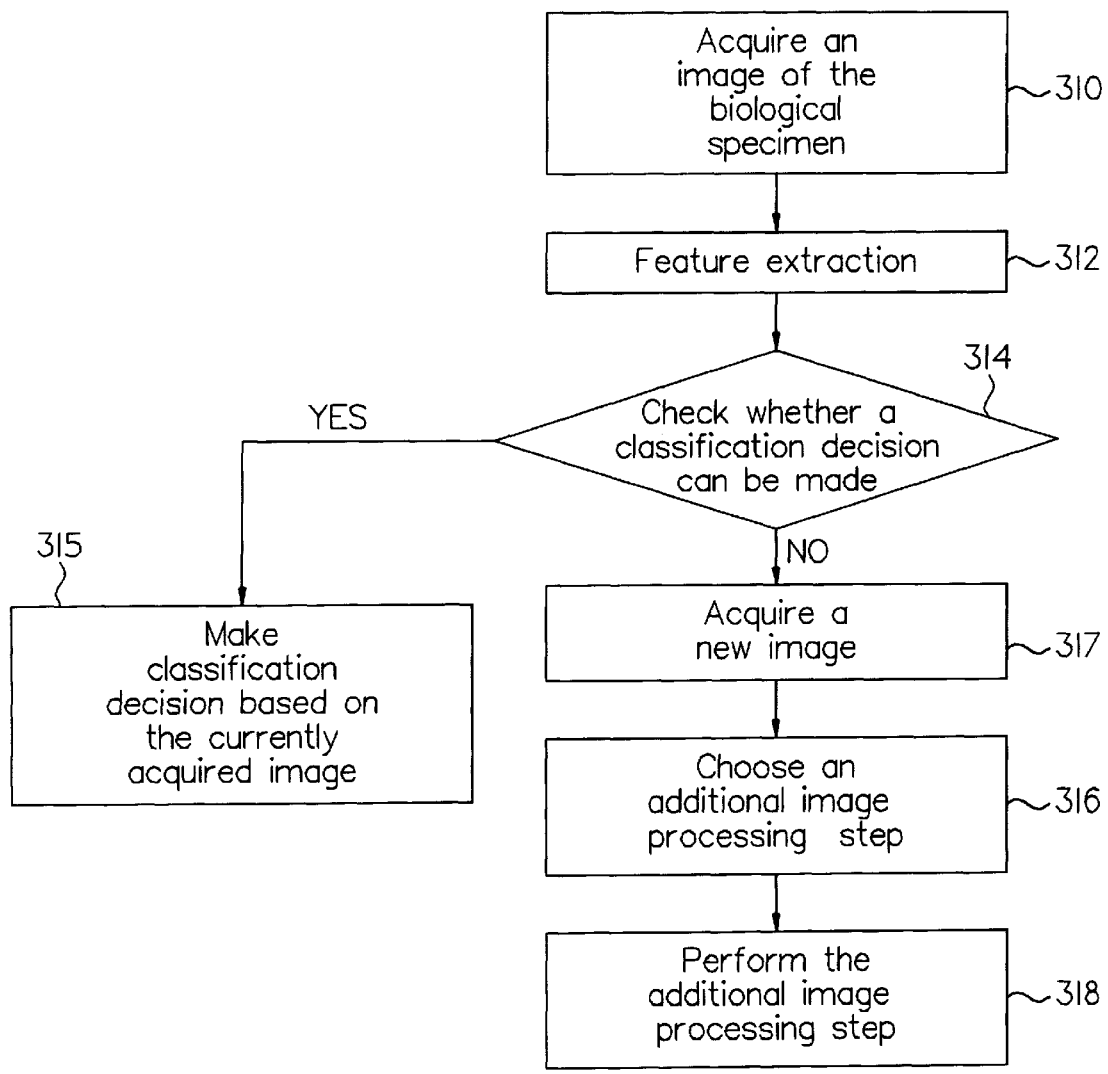
FIG. 6 shows the method of the invention to decide whether or not to acquire another image of the biological specimen.

Refer now to FIG. 6 which shows the method of the invention to decide whether or not to acquire another image of the biological specimen. The method starts in step 310 where an image of the biological specimen is acquired. The process then flows to step 312 to extract a feature from the image of the biological specimen. The process then flows to step 314 to check whether or not a classification decision can be made. If a classification decision can be made, the method of the invention flows to step 315 to make the classification decision based on the currently acquired image. If a classification decision can not be made then the method acquires an additional image in step 317. The process then flows to step 316 to choose an additional image processing step. In step 318, the additional image processing step is performed on the newly acquired image. The additional image processing module chosen in step 316 is similar to the additional image processing modules referenced in FIGS. 4A, 4B and 5 as well as additional image processing modules.

Refer now to FIG. 9, which shows the method of the invention to rescan and process certain areas using different image processing steps. The method starts with step 340 to scan and process images based on a current prioritized scan sequence. If a classification decision can be made in step 342, the process flows to step 344 to make the slide classification decision and terminate slide processing. If a classification decision can not be made in step 342, then the method of the invention flows to step 343 to determine whether or not to change the current prioritized image scan sequence. If the current prioritized image scan sequence is not to be changed, the process flows to step 341 to follow the current sequence, otherwise the process flows to step 346 where the current prioritized image scan sequence is changed to a new prioritized scan sequence. The process then flows to step 347 to determine whether a subset of image processing steps should be disabled. If so, the method of the invention disables a subset of image processing steps in step 348, otherwise the existing image processing steps are used in step 345. The process then flows to step 349 to check if additional image processing steps should be enabled. If so, the method of the invention enables a new set of image processing steps in step 350, otherwise the current processing steps are used in step 351. In step 352, the method of the invention rescans and processes areas using the current image processing steps.

In a presently preferred embodiment of the invention, the system disclosed herein is used in a system for analyzing cervical pap smears, such as that shown and disclosed in U.S. Pat. No. 5,787,188, issued Jul. 28, 1998 to Nelson et al., entitled "METHOD FOR IDENTIFYING NORMAL BIOMEDICAL SPECIMENS", which is a file wrapper continuation of abandoned U.S. patent application Ser. No. 07/838,064, filed Feb. 18, 1992; U.S. Pat. No. 5,528,703, issued Jun. 18, 1996 to Lee et al., entitled "METHOD FOR IDENTIFYING OBJECTS USING DATA PROCESSING TECHNIQUES" which is a file wrapper continuation of abandoned U.S. patent application Ser. No. 07/838,395, filed Feb. 18, 1992; U.S. Pat. No. 5,315,700, issued May 24, 1994 to Johnston et al., entitled "METHOD AND APPARATUS FOR RAPIDLY PROCESSING DATA SEQUENCES"; U.S. Pat. No. 5,361,140, issued Nov. 1, 1994 to Hayenga et al., entitled "METHOD AND APPARATUS FOR DYNAMIC CORRECTION OF MICROSCOPIC IMAGE SIGNALS"; and U.S. Pat. No. 5,912,699, issued Jun. 15, 1999 to Hayenga et al., entitled "METHOD AND APPARATUS FOR RAPID CAPTURE OF FOCUSED MICROSCOPIC IMAGES" which is a continuation-in-part of abandoned U.S. patent application Ser. No. 07/838,063, filed Feb. 18, 1992, the disclosures of which are incorporated herein, in their entirety, by the foregoing references thereto.

Now refer to FIGS. 3A, 3B and 3C which show a schematic diagram of one embodiment of the apparatus of the invention for dynamic control of slide processing 500. The apparatus of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to the CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510. In some embodiments, optics 510 may comprise color filters. In one embodiment of the invention, the optics may further comprise an automated microscope 511. The illuminator 508 provides illumination of a slide. The image capture and focus system 516 provides data to a VME bus 538. The VME bus distributes the data to an image processing system 536. The image processing system 536 is comprised of field-of-view processors 568. The images are sent along the image bus 564 from the image capture and focus system 516. A central processor 540 controls the operation of the invention through the VME bus 538. In one embodiment, the central processor 562 comprises a MOTOROLA 68030 CPU. The motion controller 504 is comprised of a tray handler 518, a microscope stage controller 520, a microscope tray controller 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet communication system 560 communicates to a workstation 542 to provide control of the system. A hard disk 544 is controlled by workstation 550. In one embodiment, workstation 550 may comprise a workstation. A tape drive 546 is connected to the workstation 550 as well as a modem 548, a monitor 552, a keyboard 554, and a mouse pointing device 556. A printer 558 is connected to the ethernet 560.

During operation, the central computer 540, running an operating system, controls the microscope 511 and the processor to acquire and digitize images from the microscope 511. The flatness of the slide may be checked, for example, by contacting the four corners of the slide using a computer controlled touch sensor. The computer 540 also controls the microscope 511 stage to position the specimen under the microscope objective, and from one to fifteen field of view (FOV) processors 568 which receive images under control of the computer 540.

It is to be understood that the various processes described herein may be implemented in software suitable for running on a digital processor. The software may be embedded, for example, in the central processor 540.

The present invention is also related to biological and cytological systems as described in the following patent applications which are assigned to the same assignee as the present invention, filed on Sep. 20, 1994 (unless otherwise noted), and which are all hereby incorporated by reference including U.S. Pat. No. 5,757,954, issued May 26, 1998 to Kuan et al entitled, "FIELD PRIORITIZATION APPARATUS AND METHOD"; U.S. Pat. No. 5,978,498, issued Nov. 2, 1999 to Wilhelm et al., entitled "APPARATUS FOR AUTOMATED IDENTIFICATION OF CELL GROUPINGS ON A BIOLOGICAL SPECIMEN" which is a file wrapper continuation of abandoned U.S. patent application Ser. No. 08/309,061; U.S. Pat. No. 5,987,158, issued Nov. 16, 1999 to Meyer et al., entitled "APPARATUS FOR AUTOMATED IDENTIFICATION OF THICK CELI GROUPINGS ON A BIOLOGICAL SPECIMEN", which is a file wrapper continuation of abandoned U.S. patent application Ser. No. 08/309,116; U.S. Pat. No. 5,787,189, issued Jul. 28, 1998 to Lee et al. entitled "BIOLOGICAL ANALYSIS SYSTEM SELF CALIBRATION APPARATUS", which is a file wrapper continuation of abandoned U.S. patent application Ser. No. 08/309,115; U.S. Pat. No. 5,828,776, issued Oct. 27, 1998 to Lee et al. entitled "APPARATUS FOR IDENTIFICATION AND INTEGRATION OF MULTIPLE CELL PATTERNS", which is a file wrapper continuation of abandoned U.S. patent application Ser. No. 08/308,992; U.S. Pat. No. 5,627,908, issued May 6, 1997 to Lee et al. entitled "METHOD FOR CYTOLOGICAI, SYSTEM DYNAMIC NORMALIZATION"; U.S. Pat. No. 5,638,459, issued Jun. 10, 1997 to Rosenlof et al. entitled "METHOD AND APPARATUS FOR DETECTING A MICROSCOPE SLIDE COVERSLIP"; U.S. Pat. No. 5,566, 249, issued Oct. 15, 1996 to Rosenlof et al. entitled "APPARATUS FOR DETECTING BUBBLES IN COVERSLIP ADHIESIVE"; U.S. Pat. No. 5,933,519, issued Aug. 3, 1999, to Lee et al. entitled "CYTOLOGICAL SLIDE SCORING APPARATUS" which is a file wrapper continuation of abandoned U.S. patent application Ser. No. 08/309, 931; U.S. Pat. No. 5,692,066, issued Nov. 25, 1997 to Lee et al. entitled "METHOD AND APPARATUS FOR IMAGE PLANE MODULATION PATTERN RECOGNITION"; U.S. Pat. No. 5,978,497, issued Nov. 2, 1999, to Lee et al. entitled "APPARATUS FOR THE IDENTIFICATION OF FREE-LYING CELLS"; U.S. Pat. No. 5,715,327, issued Feb. 3, 1998 to Wilhelm et al., entitled "METHOD AND APPARATUS FOR DETECTION OF UNSUITABLE CONDITIONS FOR AUTOMATED CYTOLOGY SCORING"; U.S. Pat. No. 5,647,025, issued Jul. 8, 1997 to Frost et al., entitled "AUTOMATIC FOCUSING OF BIOMEDICAL SPECIMENS APPARATUS"; U.S. Pat. No. 5,677,762, issued Oct. 14, 1997 to Ortyn et al., entitled "APPARATUS FOR ILLUMINATION STABILIZATION AND HOMOGENIZATION", which is a file wrapper continuation of abandoned U.S. patent application Ser. No. 08/309, 064; U.S. Pat. No. 5,875,258, issued Feb. 23, 1999 to Ortyn et al, entitled "BIOLOGICAL SPECIMEN ANALYSIS SYSTEM PROCESSING INTEGRITY CHECKING APPARATUS", which is a file wrapper continuation of abandoned U.S. patent application Ser. No. 08/309,249; U.S. Pat. No. 5,581,631, issued Dec. 3, 1996 to Ortyn et al., entitled "CYTOLOGICAL SYSTEM IMAGE COLLECTION INTEGRITY CHECKING APPARATUS"; U.S. Pat. No. 5,557,097, issued Sep. 17, 1996 to Ortyn et al., entitled "CYTOLOGICAL SYSTEM AUTOFOCUS INTEGRITY CHECKING APPARATUS"; U.S. Pat. No. 5,787,189, issued Jul. 28, 1998 to Lee et al., entitled "BIOLOGICAL ANALYSIS SYSTEM SELF CALIBRATION APPARATUS", which is a file wrapper continuation of abandoned U.S. patent application Ser. No. 08/309,115; U.S. Pat. No. 5,740,269, issued Apr. 14, 1998 to Oh et al., entitled "A METHOD AND APPARATUS FOR ROBUST BIOLOGICAL SPECIMEN CLASSIFICATION"; U.S. Pat. No. 5,797,130, issued Aug. 18, 1998 to Nelson et al., entitled "METHOD FOR TESTING PROFICIENCY IN SCREENING IMAGES OF BIOLOGICAL SLIDES" which is a file wrapper continuation of abandoned U.S. patent application Ser. No. 08/153,293 filed Nov. 16, 1993; pending U.S. patent application Ser. No. 08/485,182 to Lee et al., filed Jun. 7, 1995, entitled "INTERACTIVE METHOD AND APPARATUS FOR SORTING BIOLOGICAL SPECIMENS"; U.S. Pat. No. 5,715,326, issued Feb. 3, 1998 Ortyn et al., entitled "CYTOLOGICAL SYSTEM ILLUMINATION INTEGRITY CHECKING APPARATUS AND METHOD"; U.S. Pat. No. 5,499,097, issued Mar. 12, 1996 to Ortyn et al., entitled "METHOD AND APPARATUS FOR CHECKING AUTOMATED OPTICAL SYSTEM PERFORMANCE REPEATABILITY"; U.S. Pat. No. 5,799,101, issued Aug. 25, 1998 to Lee et al., entitled "METHOD AND APPARATUS FOR HIGHLY EFFICIENT COMPUTER AIDED SCREENING", which is a file wrapper continuation of abandoned U.S. patent application Ser. No. 08/315,719, filed Sep. 30, 1994; U.S. Pat. No. 5,787,208, issued Jul. 28, 1998 to Oh et al., entitled "IMAGE ENHANCEMENT METHOD AND APPARATUS"; U.S. Pat. No. 5,625,706, issued Apr. 29, 1997 to Lee et al., entitled "METHOD AND APPARATUS FOR CONTINUOUSLY MONITORING AND FORFCASTING SLIDE AND SPECIMEN PREPARATION FOR A BIOLOGICAL SPE EIMEN POPULATION"; U.S. Pat. No. 5,745,601, issued Apr. 28, 1998 to Lee et al., entitled "ROBUSTNESS OF CLASSIFICATION MEASUREMENT APPARATUS AND METHOD"; U.S. Pat. No. 5,671,288, issued Sep. 23, 1997 to Wilhelm et al., entitled "METHOD AND APPARATUS FOR ASSESSING SLIDE AND SPECIMEN PREPARATION QUALITY"; U.S. Pat. No. 5,621,519, issued Apr. 15, 1997 to Frost et al., entitled "IMAGING SYSTEM TRANSFER FUCNCTIO CONTROL METHOD AND APPARATUS"; U.S. Pat. No. 5,619,428, issued Apr. 8, 1997 to Lee et al., entitled "METHOD AND APPARATUS FOR INTEGRATING AN AUTOMATED SYSTEM TO A LABORATORY"; U.S. Pat. No. 5,781,667, issued Jul. 14, 1998 to Schimidt et al., entitled "APPARATUS FOR HIGH SPEED MORPHOLOGICAL PROCESSING" and U.S. Pat. No. 5,642,433, issued Jun. 24, 1997 to Lee et al, entitled "METHOD AND APPARATUS FOR IMAGE CONTRAST QUALITY EVALUATION".

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An automated cytological analysis screening method for characterizing a biological specimen comprising the steps of:

(a) acquiring an image data set representative of an image of a biological specimen within a field of view of said specimen, wherein said selected image is selected in accordance with a predetermine scan sequence of fields of view of said biological specimen;

(b) operating on said image data in accordance with a first image processing module for determining a first feature set having at least a one measurement value, M1, indicative of the magnitude of presence of at least a first feature, F1, of said selected image;

(c) selectively, in response to said first feature set, executing step (x)

operating on said image data by at least one different image processing module selected from a plurality of image processing modules, N, for determining a second feature set including at least one additional measurement value representative of a corresponding image feature, where said selected image processing module is selected based on said first feature set, and selectively executing step (x) in response to said second feature set;

operating on said image data by other processing modules selected from a plurality of image processing modules, N, for determining other measurement values representative of a corresponding image features, where said selected image processing modules are selected based on previously obtained feature set results of a previously image data set of a previous field of view;

selectively changing said selected scanning sequence and performing steps (a), (b), and (c), and repeating step (a) if images remain, otherwise terminate analysis of said biological specimen; and (d) characterizing said biological specimen and terminate further image processing of said biological specimen.

2. The method of claim 1 further includes the step of:
   operating on said image data by at least another different image processing module selected from said plurality of image processing modules for determining an additional feature set including at least one additional measurement value representative of a corresponding image feature, where said selected image processing module is selected based on feature set results of at least two different images corresponding to two different fields of view, respectively.

3. The method of claim 1 further includes the step of:
   terminating operating on said image data set by previously selected ones of said processing modules based on said feature set of a previously processed image and a last obtained feature set result of a current image data set.

4. The method of claim 1 further including the step of separately accumulating selected measurement values associated with mutually exclusive features, and analyzing said accumulated measurement values for subsequent decision making to selectively terminate or continue image processing.

5. The method of claim 1 wherein said plurality image processing modules include a group of modules consisting of a single cell classification module, a group classification module, a thick group classification module, an endocervical classification module, a cellular object classification module, and a poly detection module.

6. A method of image processing a biological specimen on a slide by an automated cytological analysis screening system for classifying a biological specimen as being normal or requiring subsequent review, where said automated cytological analysis screening system includes a plurality of unique image processing modules where each image processing module serves to determine a measurement value indicative of a unique feature of a processed image, said method comprising the steps of:

(a) image scanning said slide so as to determine a prioritization scan sequence identifying those areas on said slide where an image scanning field of view of those areas have selected cellular characteristics indicative of a likelihood of abnormal cells;

(b) fetching, in accordance with said prioritized scan sequence, an image data set representative of an image in a field of view;

(c) image processing said image data set for determining a first feature set, including at least one feature, where said feature set is representative of presence of any selected feature in the acquired image data set;

(d) selectively, in response to said feature set, executing step (x), opeating on said image data set by first selected additional ones of said plurality of unique image processing modules, for determining a second feature set, where said selected image processing modules are selected based on said first feature set, and choosing to go to step (x), or go to another image processing step based on said second feature set;

enabling and disabling selected ones of said plurality of processing modules in response to said first feature set, operating on said image data set by enabled additional selected ones of said plurality of processing modules, determining a second feature set including at least a measurement value associated with at least one feature, and choosing to go to step (x), or go to sstep (b) so as to acquire image data set associated with the next field of view in accordance with said prioritized scan sequence;

selectively changing said prioritization scan sequence and repeating above steps (b), (c), and (d);and (e) characterize said biological specimen as abnormal and terminate image fetching and image processing further fields of view.

7. The method of claim 6 further includes the step of:

selectively enabling and disabling second addition selected ones of said plurality of processing modules in response to said second feature set selectively based on said feature sets based on image data associated with two sequential ones of said field of view;

operating on said image data by said enabled second additional selected ones of said plurality of processing modules, and choosing, based on a feature set associated with said enabled second additional set of processing modules to go to step (x), or go to the (b) so as to acquire image data associated with the next field of view in accordance with said prioritized scan sequence.

8. The method of claim 6 further includes the step of separately accumulating selected measurement values associated with mutually exclusive features, and determining after each fetching of an image data set associated with an individual field of view whether to continue processing images, terminate image processing and characterize said specimen as being normal or needing review.

9. The method of claim 6 wherein said plurality image processing modules include at least a group of modules consisting of a single cell classification module, a group classification module, a thick group classification module, an endocervical classification module, a cellular object classification module, and a poly detection module.

10. The method of claim 6 wherein said selected prioritization scan sequence is a function of the quantity of endocervical cell groups and abnormal or glandular cells, where said prioritization scan sequence begins with those having high score values of both endocervical cell groups and abnormal or glandular cells.

11. The method of claim 6 wherein said selected prioritization scan sequence is selected as a function of (i) a Group Score, Z, indicative of the quantity of endocervical cells, and a SIL Score, A, indicative of the quantity of abnormal or glandular cells, determined to be present in an image of a field of view.

12. The method of claim 11 wherein said selected prioritization scan sequence is selectively chosen from the group where, (i) highest priority is assigned to those field of views having both a high Group Score and a high SIL score, (ii) highest priority is assigned to those field of views having a high Group Score, or (iii) highest priority is assigned to those field of views having a high SIL Score.

13. The method of claim 11 further where, a selected one image processing module determines (i) a Group Score, Z, indicative of the quantity of endocervical cells, and a SIL Score, A, indicative of the quantity of abnormal or glandular cells, within a processed image of a filed of view, and step (c) includes the step of comparing said Group Score Z to a predetermined threshold $Z_{th}$, and comparing said SIL Score to a predetermined threshold $A_{th}$, and selectively choosing said selected prioritization scan sequence based on said threshold comparisons.

14. The method of claim 12 wherein said selected prioritization scan sequence is selectively chosen from the group where, (iv) highest priority is assigned to those field of views having both a high Group Score and a high SIL score, (v) highest priority is assigned to those field of views having a high Group Score, or (vi) highest priority is assigned to those field of views having a high SIL Score.

* * * * *